US009034012B2

(12) United States Patent
Knoell

(10) Patent No.: US 9,034,012 B2
(45) Date of Patent: May 19, 2015

(54) LATTICE STITCH AND SURGICAL TENSION LIMITING DEVICE

(76) Inventor: Keith A. Knoell, Crozet, VA (US)

( * ) Notice: Subject to any disclaimer, the term of this patent is extended or adjusted under 35 U.S.C. 154(b) by 138 days.

(21) Appl. No.: 13/160,651

(22) Filed: Jun. 15, 2011

(65) Prior Publication Data

US 2012/0071903 A1  Mar. 22, 2012

Related U.S. Application Data

(60) Provisional application No. 61/383,527, filed on Sep. 16, 2010, provisional application No. 61/384,349, filed on Sep. 20, 2010.

(51) Int. Cl.
*A61B 17/04* (2006.01)

(52) U.S. Cl.
CPC ......... *A61B 17/0401* (2013.01); *A61B 17/0466* (2013.01); *A61B 2017/0404* (2013.01); *A61B 2017/0406* (2013.01); *A61B 2017/0464* (2013.01)

(58) Field of Classification Search
USPC ......... 606/139, 148, 213–217, 228, 232, 233, 606/144; 206/63.3, 339; 128/898; 289/1.2
See application file for complete search history.

(56) References Cited

U.S. PATENT DOCUMENTS

| | | | |
|---|---|---|---|
| 2,199,025 A * | 4/1940 | Conn | 606/232 |
| 3,664,345 A | 5/1972 | Dabbs et al. | |
| 4,275,736 A * | 6/1981 | Chodorow et al. | 606/233 |
| 4,773,421 A * | 9/1988 | Davis | 606/233 |
| 5,127,412 A | 7/1992 | Cosmetto et al. | |
| 6,030,410 A * | 2/2000 | Zurbrugg | 606/219 |
| 6,063,106 A | 5/2000 | Gibson | |
| 6,120,525 A | 9/2000 | Westcott | |

(Continued)

FOREIGN PATENT DOCUMENTS

GB  2364246 A  1/2002

OTHER PUBLICATIONS

Wheeland, Ronald G., editor. Cutaneous Surgery, "Advanced Suturing Techniques and Layered Closures", 1994, pp. 304-317, W.B. Saunders, Philadelphia, PA.

(Continued)

*Primary Examiner* — Elizabeth Houston
*Assistant Examiner* — Robert Lynch
(74) *Attorney, Agent, or Firm* — Sughrue Mion, PLLC

(57) ABSTRACT

A lattice stitch and stitching method for closing wounds are characterized by the use of a tension limiting device. First and second anchor stitches are arranged in a tissue layer spaced from and generally parallel to the wound, with the first and second anchor stitches being on opposite sides of the wound. A closing stitch is looped around the fist and second anchor stitches and tied to draw the wound to a closed condition. The tension limiting device is used during stitching of the anchor stitches. The device is arranged between the anchor stitches and the tissue layer adjacent to the wound to prevent over-tightening of the anchor stitches and lend support to the closure. The tension limiting device can be used in any soft tissue surgical application to displace and disperse suture tension at the surface of the underlying soft tissue, to fasten a dressing to the surface of a wound, and to bolster skin graft repairs of wounds.

52 Claims, 11 Drawing Sheets

(56) References Cited

U.S. PATENT DOCUMENTS

| | | | |
|---|---|---|---|
| 6,471,715 | B1 | 10/2002 | Weiss |
| 2003/0092969 | A1 | 5/2003 | O'Malley et al. |
| 2004/0254609 | A1* | 12/2004 | Esplin .................. 606/232 |
| 2005/0187577 | A1 | 8/2005 | Selvitelli et al. |
| 2005/0240221 | A1* | 10/2005 | Dunshee .................. 606/215 |
| 2006/0282119 | A1* | 12/2006 | Perchik .................. 606/232 |
| 2007/0156245 | A1* | 7/2007 | Cauthen et al. .......... 623/17.16 |
| 2008/0262543 | A1 | 10/2008 | Bangera et al. |
| 2009/0149869 | A1 | 6/2009 | Bolhum |
| 2009/0281569 | A1 | 11/2009 | Alghamdi |
| 2009/0312776 | A1* | 12/2009 | Kaiser et al. ............ 606/148 |

OTHER PUBLICATIONS

Wheeland, Ronald G., editor. Cutaneous Surgery, "Management of Surgical Complications and Suboptimal Results", 1994, pp. 929-930, 934, W.B. Saunders, Philadelphia, PA.

Nagasao T, et al, "A tie-over with 'untied' parallel stitches: A useful techique for fixation of a bolster after treatment of cryptotia." Scandinavian Journal of Plastic and Reconstructive Surgery and Hand Surgery, 2007, pp. 88-92, vol. 41, issue 2, Informa Healthcare, London, UK.

Knoell, Keith A., "The lattice stitch technique," Archives of Dermatology, Jan. 2011, pp. 17-20, vol. 147, No. 1, American Medical Association.

* cited by examiner

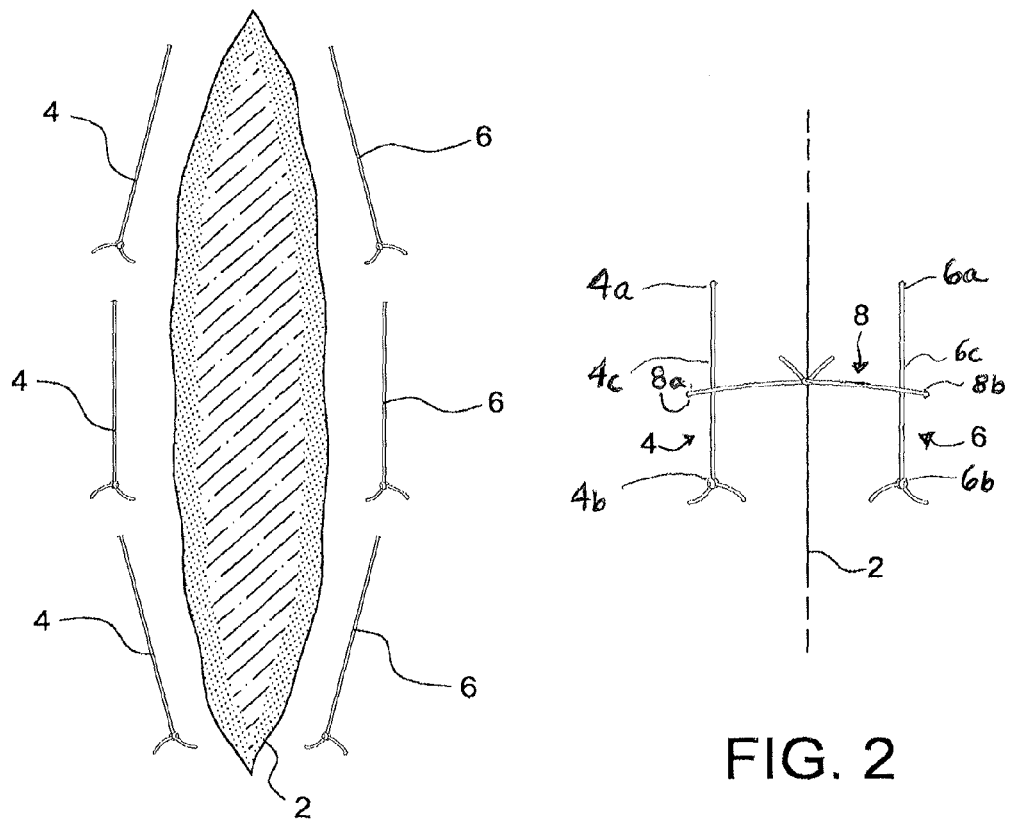
FIG. 1
FIG. 2
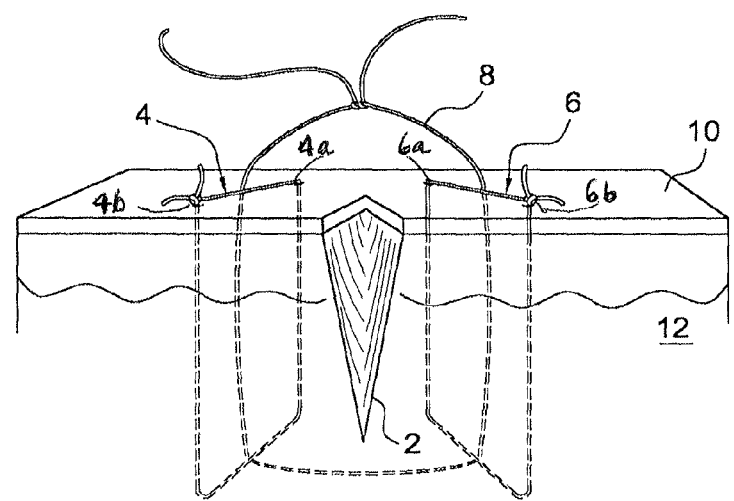
FIG. 3

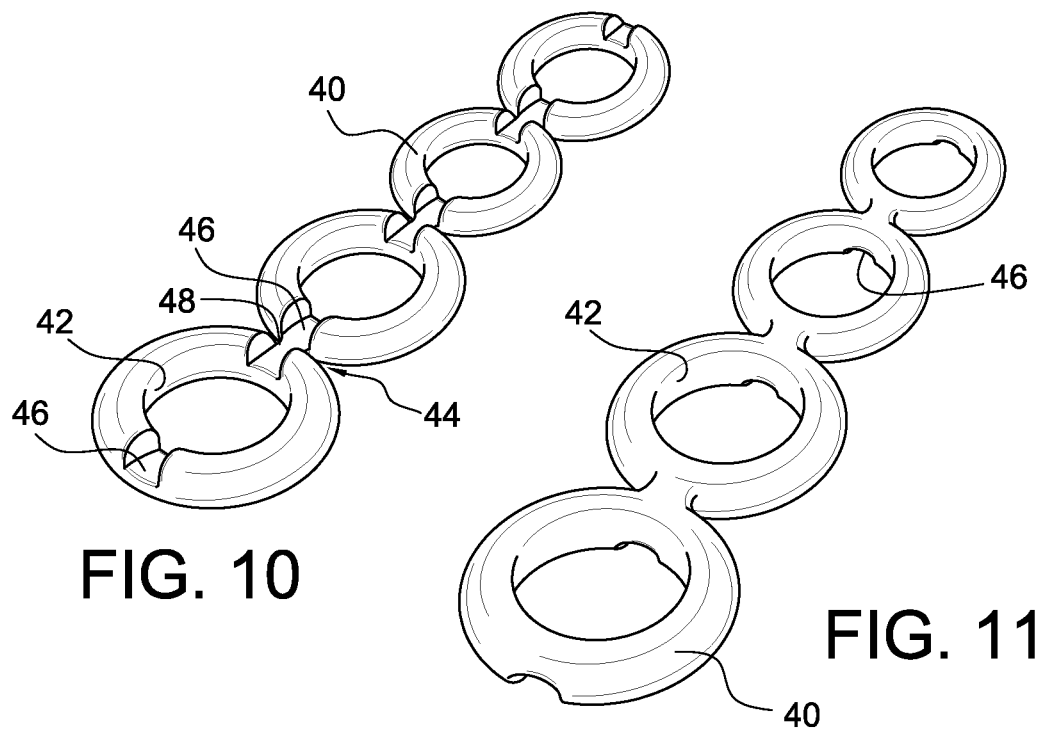
FIG. 10
FIG. 11
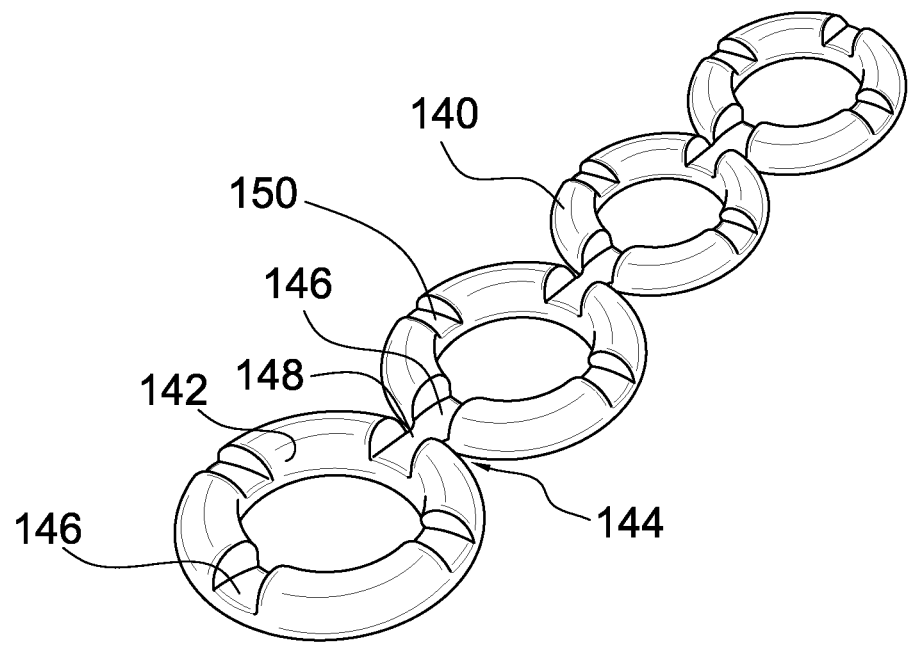
FIG. 12

LATTICE STITCH AND SURGICAL TENSION LIMITING DEVICE

This application claims the benefit of U.S. provisional patent application No. 61/383,527 filed Sep. 16, 2010 and U.S. provisional patent application No. 61/384,349 filed Sep. 20, 2010.

BACKGROUND OF THE INVENTION

Tissue tension in surgical procedures involving soft tissues can lead to many undesirable complications. Major complications in the surgical repair of wounds under tension include tissue tears, ischemia, necrosis and dehiscence. Suture tension in any cutaneous procedure can contribute to hypertrophic scar formation from stitch pressure at the surface of the skin. Primary closure of severely atrophic skin under tension, no matter how slight, is often difficult due to extreme fragility of the tissue, which can lead to tissue tears and failure of the repair. Suture tension in high tension closures can cause stitches to settle into the skin during healing making stitch removal difficult. All wounds under excessive tension are subject to a high incidence of ischemia, necrosis and dehiscence; and, as a consequence, poor healing. Tension contributes to tissue ischemia, necrosis and dehiscence through reduction of blood supply to the healing tissues by tamponade which may reduce tissue viability and the strength of the resultant scar.

Existing surgical techniques and devices are often inefficient in the dispersion of tissue tension within soft tissues and consequently can fail in applications where dispersion of tension is necessary to avoid surgical complications. In repairs of atrophic tissues, single axis stitches (simple interrupted and vertical mattress stitches) concentrate the force of closure in a plane perpendicular to the wound and predispose the tissue to tears in the axis of closure. Multi-axis stitches such as the horizontal mattress stitch or parallel stitch do not support a repair throughout the full thickness of the wound and pull directly against the skin during closure resulting in a high degree of wound instability and tissue shear. Inflexible materials such as wire or staples can often result in an unacceptably high degree of tissue shear in certain closures and cannot be used in the repair of atrophic skin. Other methods of surgical repair commonly lack the strength (simple interrupted stitch) leverage (simple interrupted, horizontal/vertical mattress, parallel stitches) stability (horizontal mattress, parallel stitch) and ability to effectively disperse tension in a direction parallel to the wound edge (all single axis closure stitches and staples) to close wounds under high tension, satisfactorily. Intra-operative strategies for reduction of ischemia, necrosis and dehiscence include partial closure repairs, secondary intention closures, placement of relaxing incisions at closure, and delay of suture removal but the disadvantages of these approaches include an increased likelihood of infection, worsening of scarring and prolonged healing time. Devices that have been designed to disperse suture tension at the surface of the skin are often cumbersome, difficult to use, limited in applied scope and may not be suited for all types of skin, including severely atrophic skin. A method that could effectively disperse tissue tension in wound repair, while minimizing these issues, would be highly desirable.

BRIEF DESCRIPTION OF THE PRIOR ART

Various stitches and stitching devices are known in the patented prior art as evidenced by the AlGhamdi US patent application publication No. 2009/0281569 and the Gibson U.S. Pat. No. 6,063,106. The AlGhamdi publication discloses a gliding stitch suturing method for closing a wound under tension, while the Gibson patent discloses a surgical spacer for preventing scarring as a result of suturing of skin tissue. More particularly, Gibson teaches a spacer including a plurality of apertures for receiving suture thread and a depression in the bottom surface thereof to space the apertures above the surface of the skin to reduce the formulation of granulation tissue.

While the prior stitches and stitching devices operate satisfactorily, they are limited in scope and are not particularly effective in closing atrophic tissues or wide wounds while avoiding tissue tears, ischemia, necrosis and/or dehiscence. The present invention was developed in order to overcome these and other drawbacks by providing a new lattice type stitch and method using a uniquely configured and versatile spacing device.

SUMMARY OF THE INVENTION

Accordingly, it is a primary object of the invention to provide a surgical lattice stitch and method for closing a wound in which a first anchor stitch is arranged in a tissue layer spaced from and generally parallel to the wound and a second anchor stitch is arranged in the tissue spaced from and generally parallel to the wound on a side of the wound opposite the first anchor stitch. A closing stitch is looped around the first and second anchor stitches and tied to draw the wound to a closed condition.

A plurality of first and second anchor stitches are provided. The anchor stitches may be arranged in an end to end configuration or they may be staggered so that the end of one anchor stitch overlaps the end of an adjacent anchor stitch. The anchor stitches may be arranged in a staggered configuration wherein the end of one anchor stitch does not overlap the end of an adjacent anchor stitch. In addition, a plurality of closing stitches may be connected between opposed pairs of first and second anchor stitches extending along the length of the wound. A plurality of second closing stitches may be provided which are tied between either an opposed pair of first and second anchor stitches or between first anchor stitches and one of the second anchor stitches other than a second anchor stitch opposite the first anchor stitches.

In order to limit the tension in the stitches, to help displace tension away from the tissues, and to enhance the fulcrum feature of the anchor stitches, a tension limiting device is provided between the anchor stitches and the tissue layer adjacent to the wound. The tension limiting device is versatile and can be used in any surgical application where displacement of suture tension from the surface of soft tissue would be desirable. In the preferred embodiment, the tension limiting device is fenestrated and formed of a solid material such as a polymer material, reinforced polymer or composite material which may be penetrated by a suture needle. The device preferably contains vertical notches spaced between the fenestrations in the periphery of the device for receiving and retaining suture thread. The device may also contain vertical notches within the fenestrations. The upper surface of the device may contain one or more longitudinal grooves that section the fenestrations to receive and retain a portion of one or more lengths of suture. The upper surface of the device may contain one or more longitudinal grooves between the fenestrations to receive and retain one or more lengths of suture. The lower surface of the device may also contain horizontal grooves between the fenestrations to help improve flexibility in the device. The edges of the device are preferably slightly rounded to reduce the sharpness. The device may be formed with a solid or composite solid/semi-solid material attached on one side that can be penetrated by a suture needle. The device may have an exterior encasement layer. The device may be impregnated with medications. The device may also have an adhesive layer. The device is preferably semi-flexible with a relatively low coefficient of friction and a semi-soft exterior surface to prevent irritation to the skin.

BRIEF DESCRIPTION OF THE FIGURES

Other objects and advantages of the invention will become apparent from a study of the following specification when viewed in the light of the accompanying drawing, in which:

FIG. 1 is a top plan view of a wound with a plurality of anchor stitches arranged on either side thereof;

FIG. 2 is a schematic illustration of a lattice stitch for closing a wound according to the invention;

FIG. 3 is a partial sectional view of the preferred embodiment of the lattice stitch of FIG. 2 relative to a wound;

FIGS. 10 and 11 are top and bottom perspective views, respectively, of a surgical tension limiting device according to the invention;

FIG. 12 is a top perspective view of an alternate embodiment of a surgical tension limiting device according to the invention;

DETAILED DESCRIPTION

Figure 4:
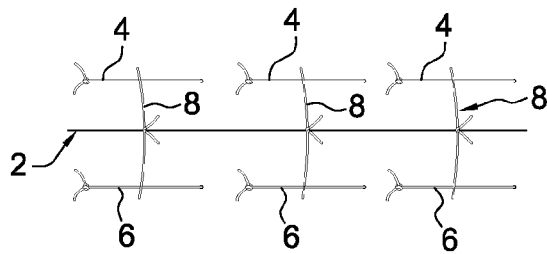
FIG. 4 is a schematic illustration of a plurality of stitches for closing a wound.

The lattice stitch according to the invention will be described with reference to FIGS. 1-3. The stitch is designed to disperse closure forces widely throughout the full thickness of a repair to a wound in both parallel and perpendicular axes. This dispersion of force results in a significant reduction of tension in the skin along the perpendicular plane of wound closure and thus facilitates satisfactory closure of the defect and better wound healing.

Referring to FIG. 1, there is shown a wound 2 in the skin tissue layer of a patient. A first anchor stitch 4 is arranged in a tissue layer spaced from and generally parallel to the wound. A second anchor stitch 6 is also arranged in the tissue layer spaced from and generally parallel to the wound on an opposite side of the wound from the first stitch. For longer wounds, a plurality of first and second anchor stitches are provided, preferably in spaced relation so that there are opposed pairs of anchor stitches as shown. As shown in FIG. 2, a closing stitch 8 is looped around the first 4 and second 6 anchor stitches and tied to draw the wound 2 to a closed condition. A single complementary pair of opposed anchor stitches 4 and 6 with a single closing stitch 8 in this configuration is described as a basic lattice stitch. The preferred stitching is a nylon monofilament material.

FIG. 3 is a partial sectional view of the lattice stitch of FIG. 2 showing how it is used to close a wound 2. The anchor stitches 4 and 6 are placed parallel and bilateral to the wound, preferably a minimum of 5 mm from the edges of the wound. For each anchor stitch, a large bite of skin and subcutis is taken. Each anchor stitch 4, 6 is bound in a closed loop on the tissue surface. The anchor stitches each penetrate the epidermis 10 and extend into the subepidermal tissue 12 of the patient. Each anchor stitch loop is defined by an anchor stitch loop entrance point portion 4a, 6a which enters at the tissue surface and an anchor stitch loop exit point portion 4b, 6b which exits out of the tissue surface, thereby defining terminal ends of the loop of each anchor stitch above the tissue surface. A connecting portion 4c, 6c of each anchor stitch is a portion located between the insertion and exit portions. In the preferred embodiment, the closing stitch 8 is looped completely around the first and second anchor stitches as shown in FIG. 3, and tied to draw the wound to a closed condition. The closing stitch also includes a loop entrance point portion 8a and a loop exit point portion 8b, thereby defining a closing stitch loop structure above the tissue surface (see FIG. 3). The closing stitch is located close to at least a part of the first connecting portion 4c of the first anchor stitch 4 at the closing stitch tissue insertion point and close to a part of the second connecting portion 6c of the second anchor stitch at the closing stitch tissue exit point to allow a conformational change in each of the first and second anchor stitches wherein at least a part of the first connecting portion of the first anchor stitch is configured to move closer to a central longitudinal axis of the wound closure than each of the terminal ends of the first anchor stitch. At least a part of the second connecting portion of the second anchor stitch is configured to move closer to the central longitudinal axis of the wound closure than at each of the terminal ends of the second anchor stitch, when the wound is drawn to the closed condition (see FIG. 2). In an alternate embodiment, the closing stitch can be looped completely around one anchor stitch, then looped around and passed through the loop of the second anchor stitch and tied to draw the wound to a closed condition. In a further embodiment, the closing stitch can be looped around and passed through the loop of each anchor stitch and tied to draw the wound to a closed condition.

Several variations of lattice closures may be provided as shown in FIGS. 4-7. Referring now to FIG. 4, a simple lattice closure will be described. This closure is formed of a plurality of basic lattice stitches adjacent to the wound 2. Each basic lattice stitch comprises an opposed pair of anchor stitches 4, 6 with a closure stitch 8 therebetween. In a simple lattice closure, the anchor stitches are arranged in spaced end-to-end configurations on opposite sides of the wound.

Figure 5:
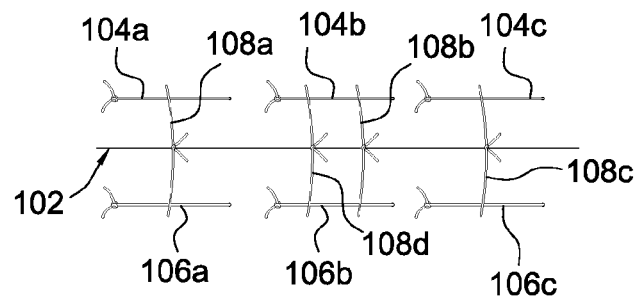
FIGS. 5-7 are schematic illustrations of alternate lattice stitching arrangements, respectively, according to the invention.

In FIG. 5, first anchor stitches 104a-c and second anchor stitches 106a-c are provided in end-to-end configurations on opposite sides of a wound 102 and tied with closing stitches 108a-c. Because the anchor stitches are fairly robust, additional closing stitches may be provided. Thus, the middle pair of anchor stitches 104b, 106b in FIG. 6 contains an additional closing stitch 108d for extra strength and support at a single closure area.

Figure 6:
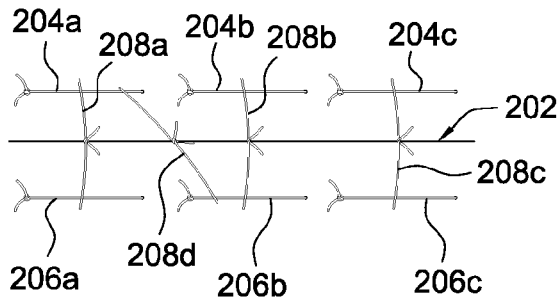

In FIG. 6, first anchor stitches 204a-c and second anchor stitches 206a-c are provided in end-to-end configuration on opposite sides of a wound 202 and tied with closing stitches 208a-c. In addition, a supplemental closing stitch 208d is tied between anchor stitches that are offset relative to the opposed pairs of anchor stitches. Thus, in FIG. 6, a supplemental closing stitch 208d is tied between a first anchor stitch 204a and a second anchor stitch 206b other than the second anchor stitch 206a opposite the first anchor stitch 204a. Such an arrangement of closing stitches can be used to close small defects and to re-align wound edges between primary basic closure points.

Figure 7:
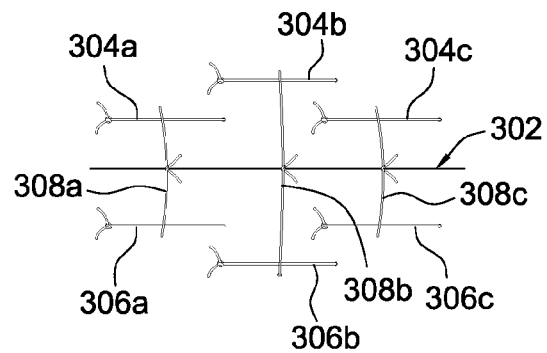

FIG. 7 illustrates a further variation of a lattice stitch closure for closing a wound 302. In this closure first anchor stitches 304a-c are set at variable distances from the wound edge compared to adjacent anchor stitches, with a slight overlap of adjacent anchor stitches. Second anchor stitches 306a-c are set at variable distances from the wound edge compared to adjacent anchor stitches, with a slight overlap of adjacent anchor stitches. Closing stitches 308a-c are tied between the opposed pairs of anchor stitches. Overlap of adjacent anchor stitches 304a-c and 306a-c increases the density of closing points and disperses forces parallel to the wound edge more widely in a non-linear fashion. This configuration of anchor stitches can be described as a near-far stacked relation.

Figure 8:
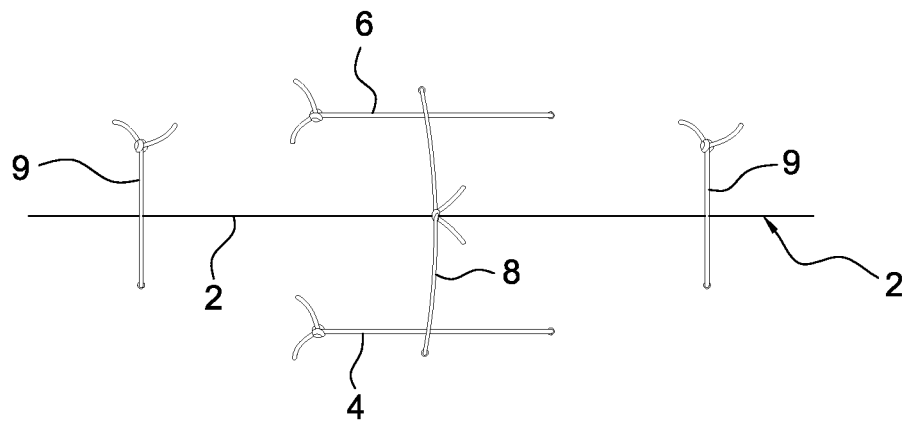
FIG. 8 is a schematic illustration of a lattice stitch used as a tension support element in a simple interrupted stitch closure.
Figure 9:
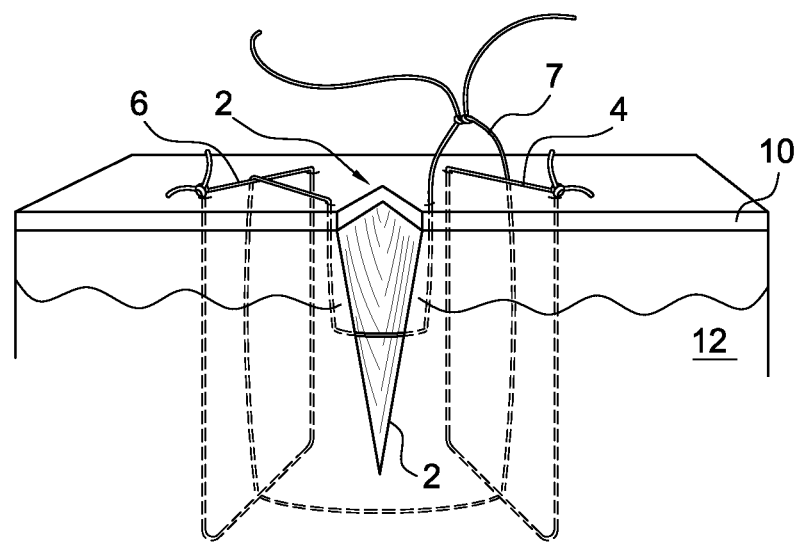
FIG. 9 is a schematic illustration of a lattice stitch using a vertical mattress stitch as the closing stitch.

It is readily apparent that a combination of lattice stitching arrangements shown in FIGS. 4-7 may be provided depending on the severity and configuration of the wound to be closed. Individual components of the lattice stitch can also used alongside other suture methods to accomplish a given closure at the discretion of the surgeon. For example, referring to FIG. 8, a basic lattice stitch 4, 6, 8 is used as a tension support element alongside two simple interrupted stitches 9. In addition, a variety of other stitches can be used as the closing stitch in a lattice closure. For example, vertical mattress sutures 7 can be used in place of simple interrupted sutures as the closing stitches to help evert wound edges as shown in FIG. 9.

Proper tensioning of the anchor stitches is vital to lattice stitch efficacy. Anchor stitches that are set excessively slack require the tissues to stretch further as tension in the closing stitch is brought to bear before force can be effectively transferred from the closing stitch to the anchor stitches. This can significantly inhibit the ability of the lattice stitch to effectively disperse tension from the tissue in the perpendicular plane of wound closure, and, in particular, can lead to tissue tear behind the anchor stitch in severely atrophic, inelastic skin. Over-tightening of the anchors, by contrast, could cause tissue ischemia. It is particularly important, yet challenging, to properly set anchor tension in atrophic skin. To facilitate proper tensioning of the anchor stitches, to help displace tension away from the surface of the tissues, to lend structural support to the lattice closure, to enhance leverage of the closing stitches over the anchor stitches, and to further reduce suture shear in the tissues and on the anchor stitches as the closing stitch is drawn over the anchor stitches, a tension limiting device is preferably provided between the anchor stitches and the tissue layer adjacent to the wound. The device is versatile and can be used in a lattice stitch closure or in any soft tissue surgical application to displace and disperse suture tension at the surface of the underlying soft tissue thereby reducing the likelihood of hypertrophic scar formation from suture tension.

The tension limiting device according to the invention will now be described with reference to FIGS. 10-25. More particularly, the device 40 has an elongated configuration and, in the preferred embodiment, contains a plurality of fenestrations 42 as shown in FIG. 10. Each fenestration preferably has a generally circular or oval configuration. The fenestrations preferably have a common major axis corresponding with the longitudinal axis of the member. The device preferably contains vertical notches 44 in the periphery of the device positioned between the fenestrations. The top surface of the device may contain aligned horizontal longitudinal grooves 46 that section the fenestrations and extend to the peripheral edges of the device as shown in FIG. 10. The top surface of the device may also contain one or more grooves 48 between fenestrations as will be developed below. The bottom surface of the device within the periphery of the fenestrations is smooth as shown in FIG. 11.

Referring to FIG. 12 a top perspective view of an alternative embodiment of the device 140 contains one or more grooves 150 that section the fenestrations 142 on the top of the device in any location except that occupied by groove 146. The device may contain one or more vertical notches 144 between the fenestrations. The top surface of the device may contain aligned horizontal longitudinal grooves 146 that section the fenestrations. The top surface of the device may also contain one or more horizontal grooves 148 between the fenestrations.

Figure 13:
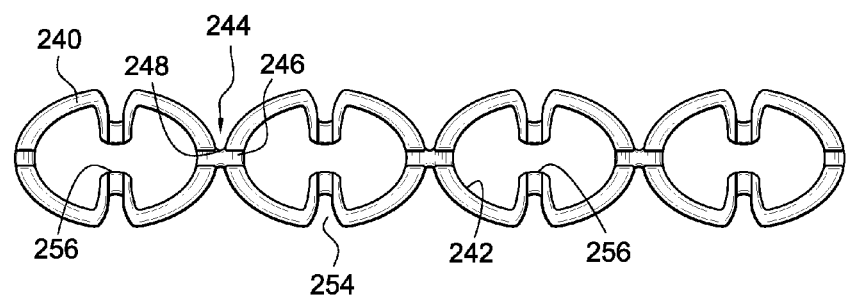
FIGS. 13 and 14 are top and bottom plan views, respectively, of a further embodiment of a surgical tension limiting device according to the invention.
Figure 14:
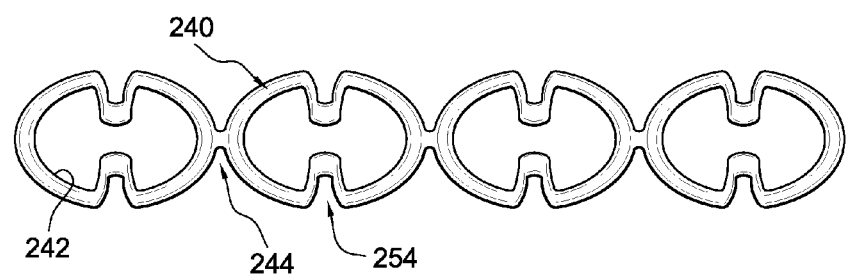

Referring to FIGS. 13 and 14, showing top and bottom plan views, respectively, of a further aspect of the invention, the device 240 contains one or more vertical notches 254 within the fenestrations 242, and may contain one or more vertical notches 244 between the fenestrations. The top surface of the device may contain one or more horizontal grooves 256 within the fenestrations, over one or more vertical notches 254. The top surface of the device may contain one or more horizontal grooves 248 between the fenestrations and may contain aligned horizontal longitudinal grooves 246 that section the fenestrations.

Figure 15:
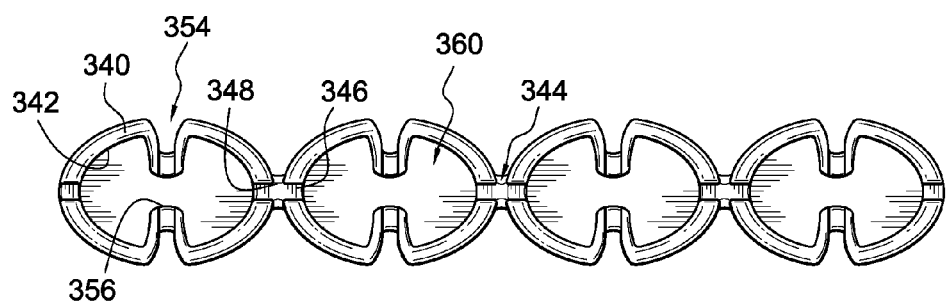
FIGS. 15 and 16 are top and bottom perspective views, respectively, of an additional embodiment of a surgical tension limiting device according to the invention.
Figure 16:
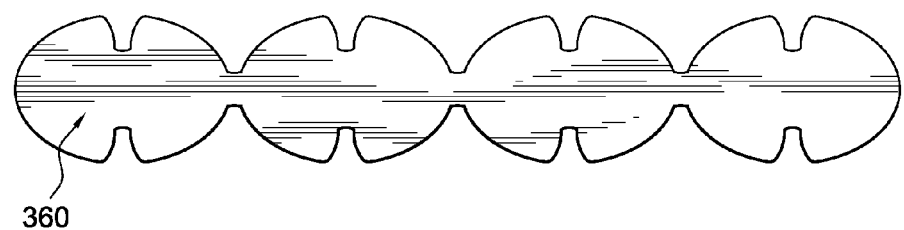

Referring to FIGS. 15 and 16 showing top and bottom plan views, respectively, of a further embodiment of the invention, the device 340 is formed of a solid material or solid/semisolid composite material 360 on the base of the device that can be penetrated by a suture needle passed through a fenestration 342 in the superstructure of the device. The material 360 on the base of the device may be dissimilar from the material forming the remainder of the device. The device may contain one or more vertical notches 354 within the fenestrations 342, and may contain one or more vertical notches 344 between the fenestrations. The top surface of the device may contain one or more horizontal grooves 356 within the fenestrations, over the one or more vertical notches 354. The top surface of the device may contain one or more horizontal grooves 348 between the fenestrations and may contain aligned horizontal longitudinal grooves 346 that section the fenestrations.

Figure 17:
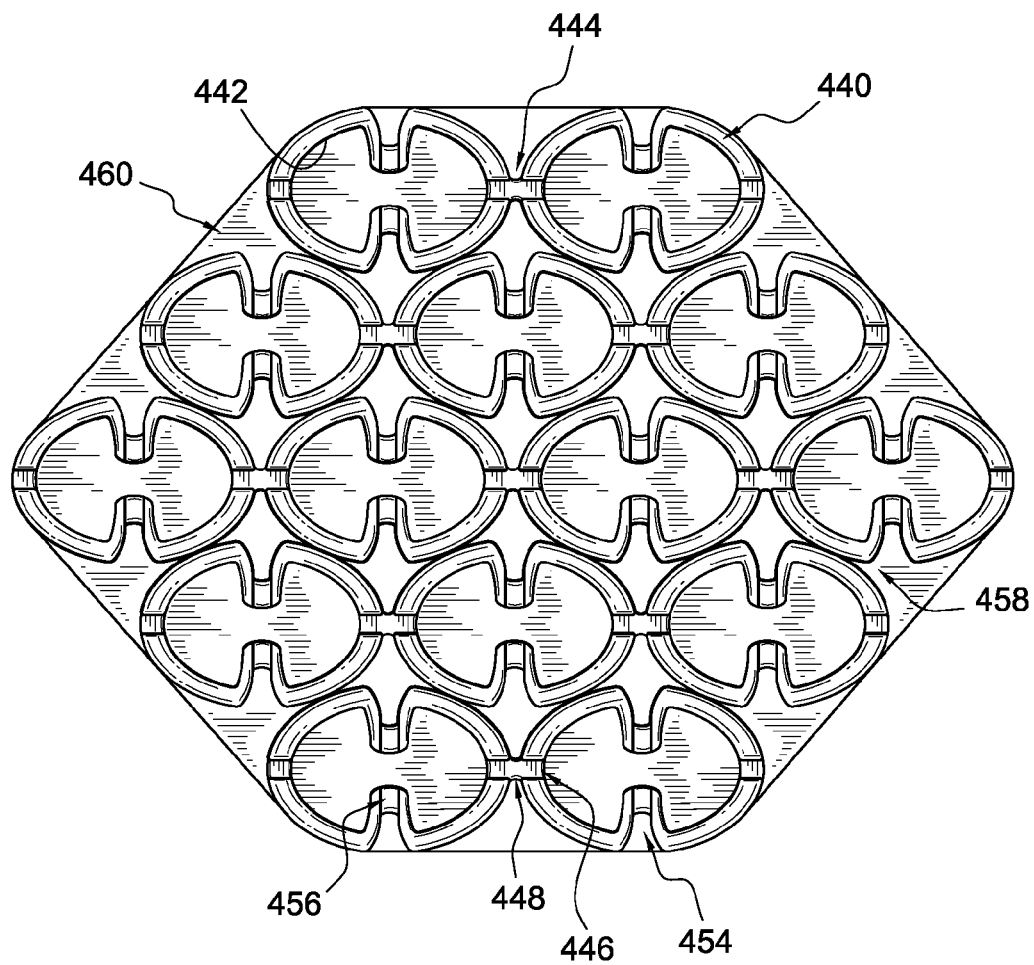
FIGS. 17 and 18 are top and side perspective views, respectively, of a further embodiment of a surgical tension limiting device according to the invention.
Figure 18:
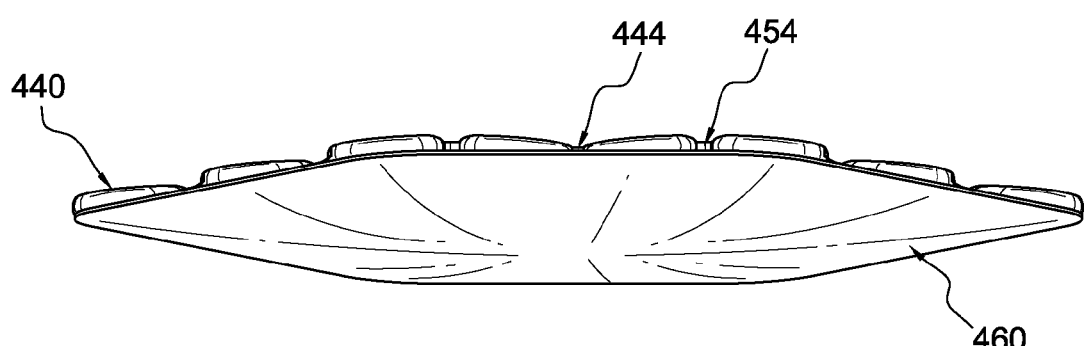

Referring to FIGS. 17 and 18, showing top and side plan views, respectively, of another aspect of the invention, a device 440 with rows of fenestrations 442 in parallel is formed of a solid material or solid/semisolid composite material 460 on the base of the device that can be penetrated by a suture needle passed through fenestration 442 in the superstructure of the device. The material 460 on the base of the device may be dissimilar from the material forming the remainder of the device. One or more vertical notches 458 is present at the junction between parallel rows of fenestrations. The device may contain one or more vertical notches 454 within the fenestrations 442 and may contain one or more vertical notches 444 between the fenestrations. The top surface of the device may contain one or more horizontal grooves 456 within the fenestrations over the one or more vertical notches 454. The top surface of the device may contain one or more horizontal grooves 448 between the fenestrations and may contain aligned horizontal longitudinal grooves 446 that section the fenestrations.

Figure 19:
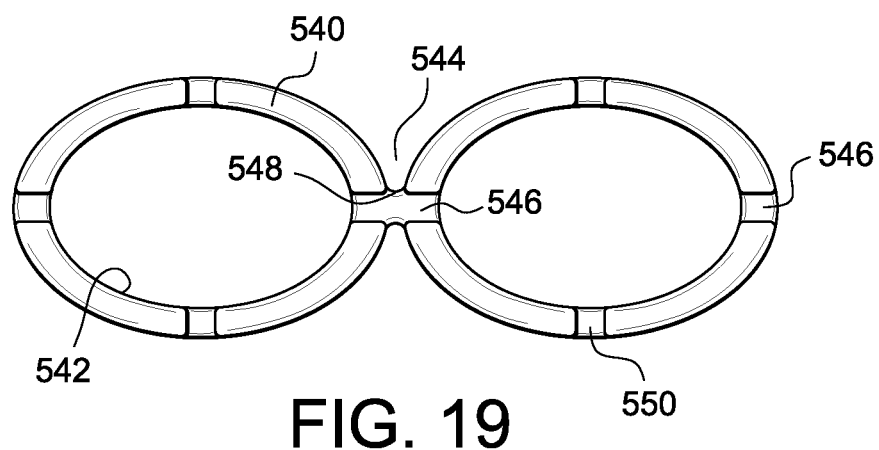
FIGS. 19-21 are top, bottom, and side plan views, respectively, of a further embodiment of a surgical tension limiting device according to the invention.
Figure 20:
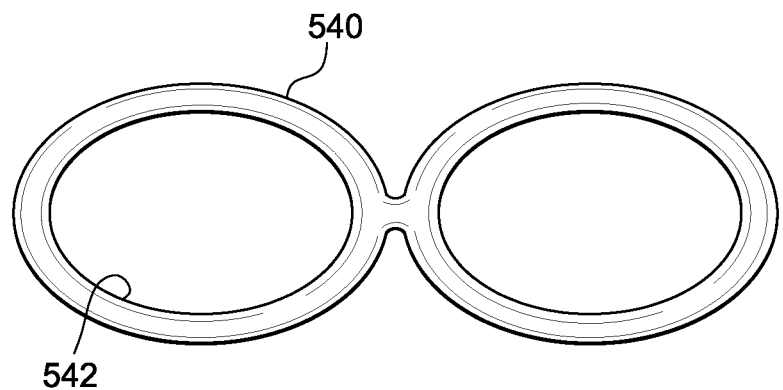
Figure 21:
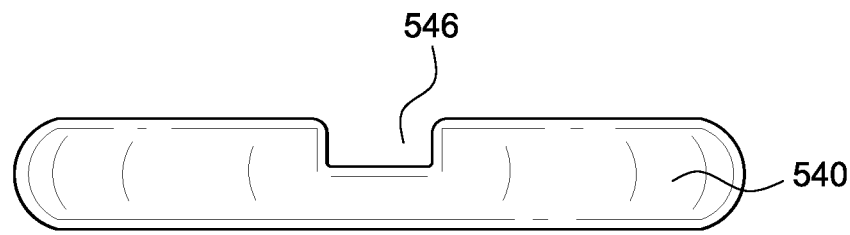

The device may be formed in any desired length with any number of fenestrations. The device may contain more than one row of fenestrations in parallel. Hence, the devices 40, 140, 240, and 340 shown in FIGS. 10-16 each have four fenestrations in a single row, device 440 shown in FIGS. 17 and 18 has fourteen fenestrations in parallel rows, and the device 540 shown in FIGS. 19-21 has two fenestrations 542. The device can be cut to size and used as the physician desires. Device 540 of FIGS. 19-21 may thus be formed independently or it may be formed by severing the device 140 of FIG. 12. As shown in FIGS. 19-21, the device 540 contains vertical notches 544 between the fenestrations, aligned horizontal longitudinal grooves 546 that section the fenestrations, horizontal grooves 548 between the fenestrations and horizontal grooves 550 within the fenestrations. Accordingly, a physician could run the device the full length of the incision, anchor with a few anchor stitches, place the lattice stitches, and then continue closures using the grooves, notches, fenestrations, or a combination of features to complete the closure.

The device is formed of a solid material which can be penetrated by a suture needle. Suitable materials include polymer material, reinforced polymer material, silicone, reinforced silicone, composite material and rubber. The edges of the device are preferably slightly rounded to reduce sharpness. Any embodiment of the device can be formed with a solid material or semi-solid/solid composite material layer attached on at least one side that can be penetrated by a suture needle. Thus, device 340 is formed with an attached solid material to the base of device 240. The device can be formed with an exterior encasement layer. The device may be impregnated with medications. The device may also be formed with an adhesive material layer. Preferably, the device is semi-flexible.

Figure 22:
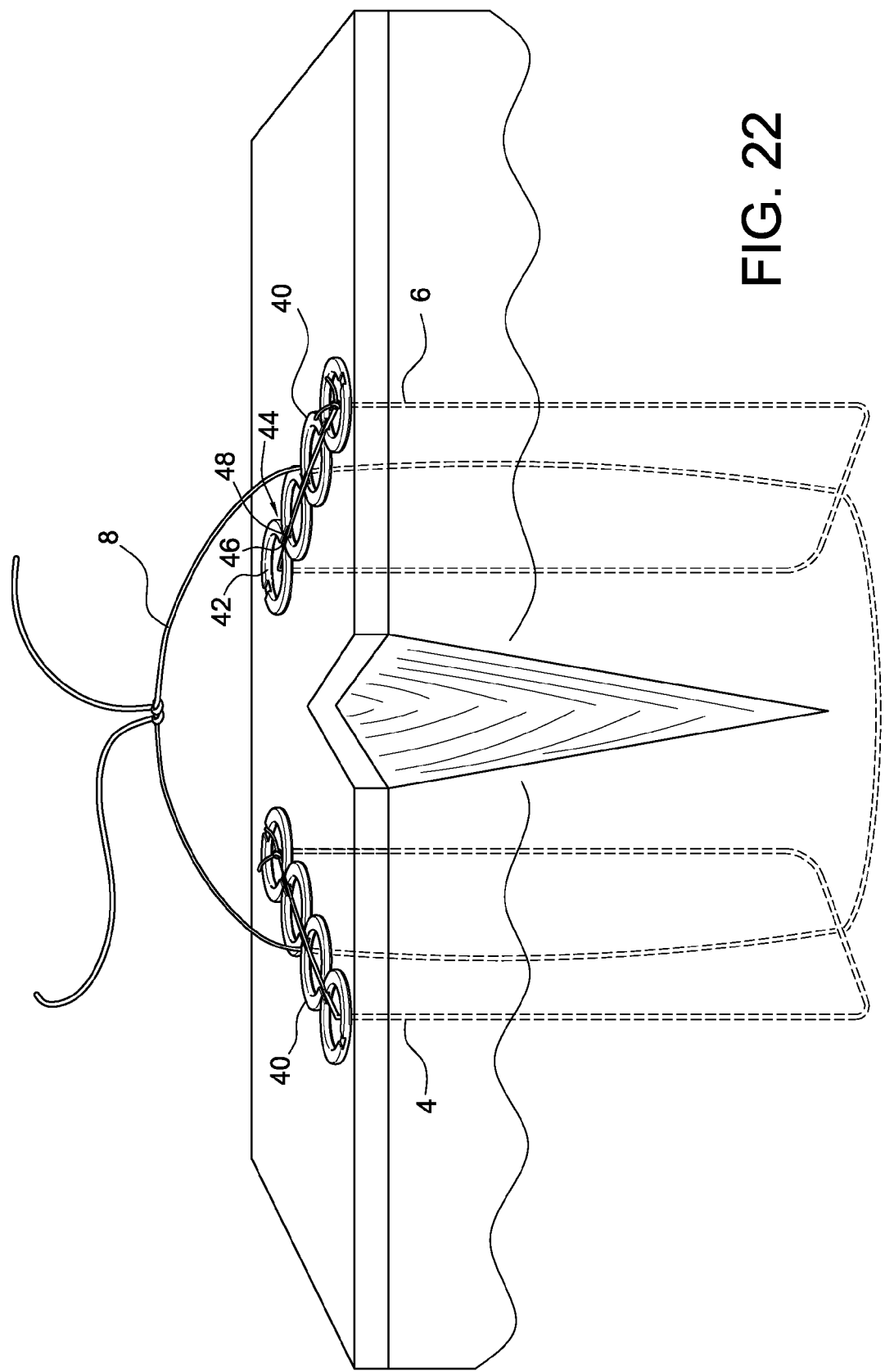
FIG. 22 is a partial sectional view of a lattice stitch including a surgical tension limiting device according to the invention.

Referring to FIG. 22, the device 40 of FIGS. 10 and 11 is placed on the skin of the patient adjacent to a wound 2. During stitching of the anchor stitches 4, 6 and with reference also to FIGS. 10 and 11, one end of the anchor stitch passes through a fenestration 42 and into a groove 46 in the upper surface of the device adjacent to the fenestration. The other end of the anchor stitch passes through an adjacent fenestration and groove and is tied. The anchor stitches are retained in the grooves of the device and hold the device in place while the device limits the tension in the anchor stitches. The device permits proper tensioning of the anchor stitches to prevent over-tightening, especially in atrophic skin, and allows otherwise firm anchor tension to optimize lattice efficacy. With the device, the surgeon can properly and consistently set anchor tension without the help of an assistant or a variable tension instrument tie. The device supports the closure by setting each closing stitch though a groove 48 and a notch 44 and providing additional strength in the anchor stitch for the closing stitch 8 to be drawn against. In a lattice closure where device 140 of FIG. 12 is used, the groove 150 can be used in place of groove 48 and notch 44 to set the closing stitch, if complementary opposed devices are placed slightly out of alignment. In a lattice closure where device 240 of FIGS. 13 and 14 is used, if complementary opposed devices are placed slightly out of alignment, notch 254 and groove 256 can be used in place of notch 244 and groove 248 to set the closing stitch. The surgeon may use any of the grooves, notches, fenestrations, or a combination of features of the device to complete the closure.

Figure 23:
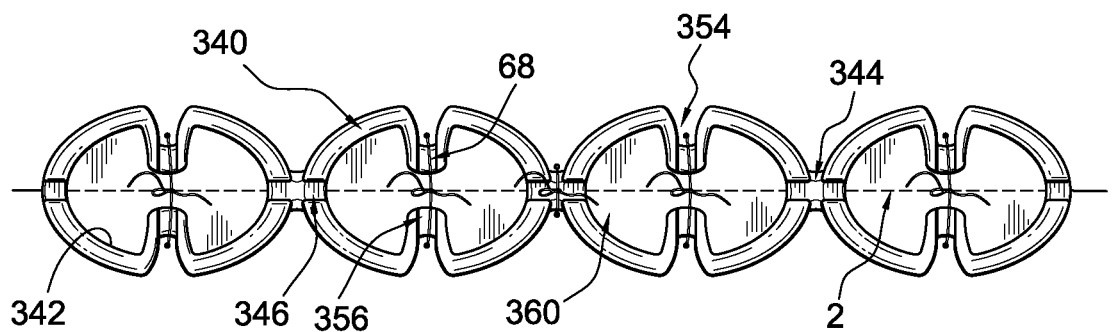
FIG. 23 is a top plan view of a simple wound repair including a surgical tension limiting device according to the invention.

The device is versatile and can be used as a means of reducing suture or staple tension at the surface of the skin in the application of simple wound repair. A reduction of tension at the surface of the skin may lessen the severity of scarring. Accordingly, in a wound repair, the device is placed over the wound, with the longitudinal axis of the device corresponding to the longitudinal axis of the wound, and a stitch or staple closure of the wound is made with the device anchored over the wound. As shown in FIG. 23, device 340 is used in this type of application, anchored over the wound 2 by a length of suture 68. The configuration of the device 340 permits a spring flexion of the device when suture placed through notch 354 and groove 356 draws the wound closed, allowing good approximation of the wound edges. The surgeon may use any of the grooves, notches, fenestrations, or a combination of features of any embodiment of the device to complete the closure.

Figure 24:
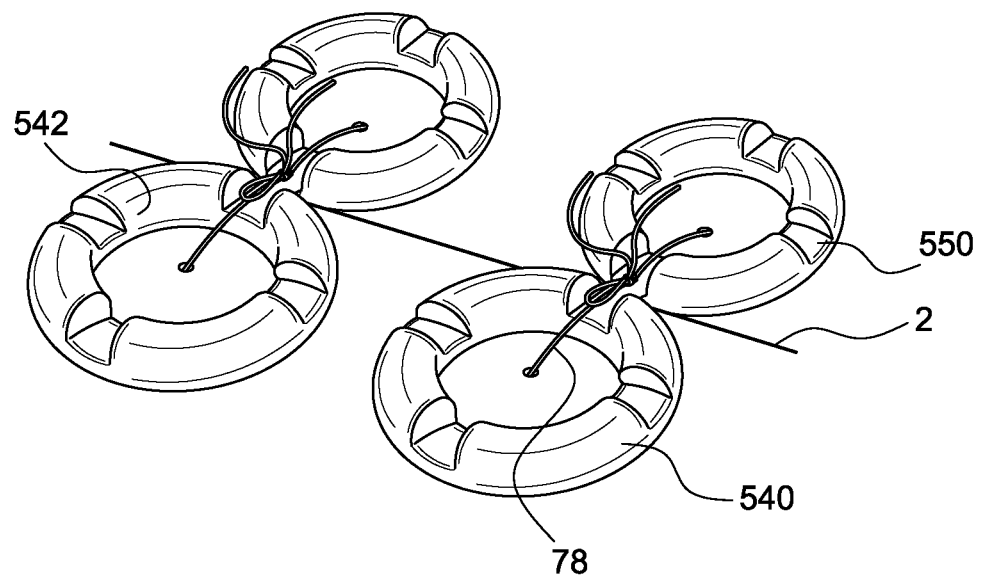
FIG. 24 is a top perspective view of an alternate simple wound repair including a surgical tension limiting device according to the invention.

In an alternate strategy of wound repair a plurality of devices 540 are placed with the longitudinal axis of each device perpendicular to the longitudinal axis of the wound as shown in FIG. 24. A stitch closure of the wound 2 is then made with each device anchored over the wound by a length of suture 78 used to close the wound. The surgeon may use any of the grooves, notches, fenestrations, or a combination of features of any embodiment of the device to complete the closure.

The device can be used as a means to fix a wound dressing to the surface of a wound. Accordingly, a wound dressing can be placed on the surface of a wound and a device is placed over the dressing and used as a means to draw the surface of the wound together while simultaneously holding the dressing in place. Staples or sutures may be used to hold the device in place over the dressing. The device can be used as a means to hold a dressing to the surface of a wound that has been closed by other means. Alternatively, a device with an integral dressing formed as a component of the device can be used as a single unit to dress the wound and draw the wound together to a closed condition. A device with an integral dressing may be used to cover the surface of a wound repaired by other means. A device with an integral dressing may be used as a bolster dressing for a skin graft repair and can be cut to fit the repair by the surgeon. A device used in the application of a bolster dressing for a tissue graft distributes tension uniformly over the surface of the graft and holds the graft securely in place. Basting stitches can be set into the graft through one or more fenestrations in the device. The surgeon may use any of the grooves, notches, fenestrations, or a combination of features of any embodiment of the device to fasten the device to the surface of the tissue. Sutures, staples or any other suitable fastening material may be used to secure the device to the surface of the tissue.

Figure 25:
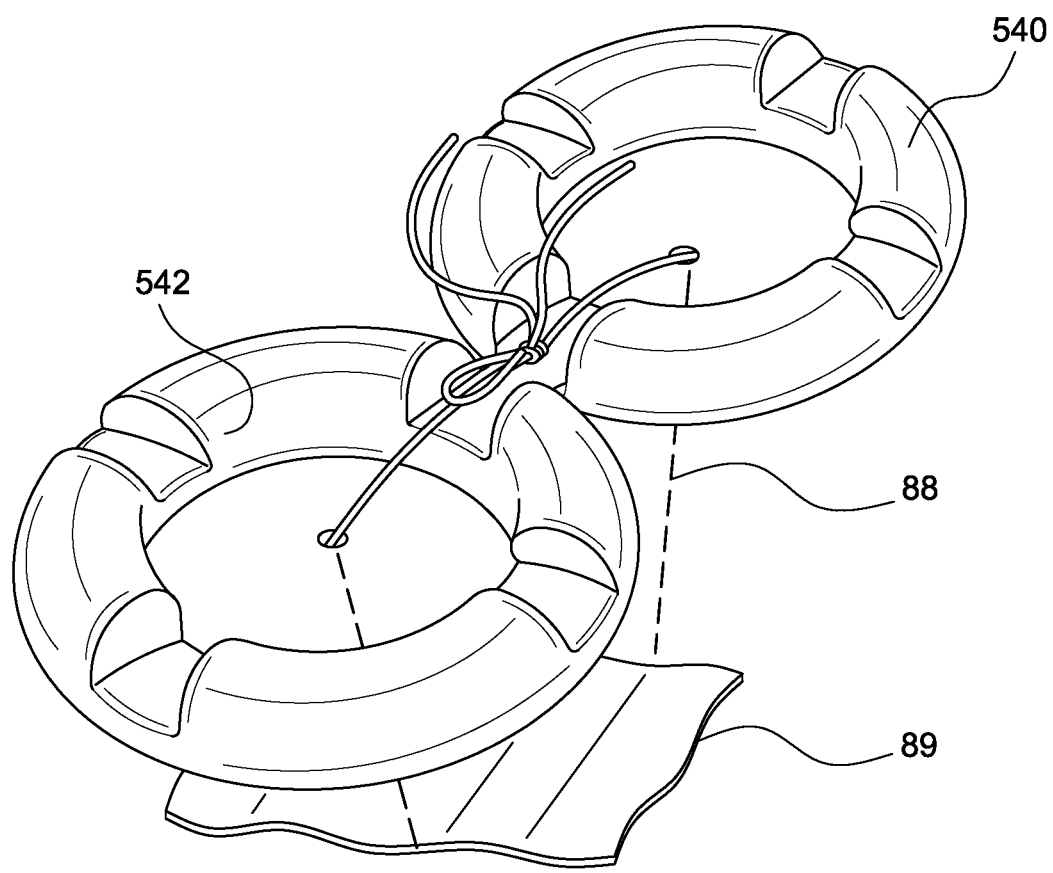
FIG. 25 is a top perspective view of a surgical tension limiting device according to the invention containing a length of suture used to secure a subcutaneous structure.

The device can be used as a means of reducing suture tension at the surface of the skin in the application of suture support of subcutaneous structures. In this application, the device 540 is anchored by the suture 88 used to support the subcutaneous structure 89 as shown in FIG. 25. Any of the grooves, notches, fenestrations, or a combination of features of any embodiment of the device can be used by the surgeon to anchor the device to the skin by the suture used to support the subcutaneous structure.

Although the provision of fenestrations in the device is preferred, a non-fenestrated tension limiting device may be provided that contains any other feature of the fenestrated embodiment of the device.

The device prevents stitches from settling in the skin during healing. Thus sutures are easily accessed during removal. The device is removed with the stitches once healing is complete.

The efficacy of a lattice stitch closure is enhanced by proper tensioning and positioning of the anchor stitches, appropriate placement of the closing stitch and the quality of suture material used in the closure. In an optimal lattice closure, the anchor stitches should be set fairly deep and wide, and with a minimum of slack, in order to effectively transfer tension in the parallel direction. The anchors should also be set far enough from the wound edge to prevent mutual contact at closure.

Proper positioning of the closing stitch near the anchor stitch will allow an efficient transfer of tension from the closing stitch to the anchor stitch, and will help prevent unnecessary stretching of the skin directly behind the closing stitch during closure. Lattice closures with slack anchors and a closing stitch placed far away from the anchors can result in a significant reduction of lattice stitch performance.

Monofilament nylon is a suitable suture material for a lattice stitch repair. This material is strong, flexible, elastic, and has a low coefficient of friction to help reduce tissue shear. It is readily available. The elastic property of nylon allows for passive tensioning adjustment of closure forces throughout the wound during the healing period, thus enhancing stability of the closure.

While the preferred forms and embodiments of the invention have been illustrated and described, it will be apparent to those of ordinary skill in the art that various changes and modifications may be made without deviating from the inventive concepts set forth above.

What is claimed is:

1. A surgical lattice stitch repair adapted for closing wounds, comprising three lengths of suture configured in the following arrangement:
   (a) a first length of suture designated as a first anchor stitch configured to be arranged in a tissue layer parallel to and apart from a plane extending vertically through a wound edge; said first anchor stitch bound in closed loop at a fastening point, said fastening point configured to be located on a tissue surface; said first anchor stitch loop defined by a first anchor stitch loop tissue insertion point portion, and a first anchor stitch loop tissue exit point portion; each of said first anchor stitch loop tissue insertion point portion and said first anchor stitch loop tissue exit portion representing a terminal end of the first anchor stitch loop on the tissue surface; said first anchor stitch loop further defined by a first connecting portion of suture located between the first anchor stitch tissue insertion point portion and the first anchor stitch tissue exit point portion;
   (b) a second length of suture designated as a second anchor stitch configured to be arranged in the tissue layer parallel to and apart from the plane extending vertically through the wound edge on an opposite side of the wound from said first anchor stitch; said second anchor stitch bound in closed loop at a second fastening point, said second fastening point configured to be located on a tissue surface; said second anchor stitch loop defined by a second anchor stitch loop tissue insertion point portion, and a second anchor stitch loop tissue exit point portion; each of said second anchor stitch loop tissue insertion point portion and said second anchor stitch loop tissue exit point portion representing a terminal end of the second anchor stitch loop on the tissue surface; said second anchor stitch loop further defined by a second connecting portion of suture located between the second anchor stitch tissue insertion point portion and the second anchor stitch tissue exit point portion; and
   (c) a third length of suture designated as a closing stitch configured to be inserted into the tissue surface at a closing stitch tissue insertion point and looped around said first and second anchor stitches in order to draw the wound to a closed condition to provide a wound closure; and
      the closing stitch configured to extend under a lowermost portion of said first anchor stitch, configured to extend across the vertical plane of the wound to the opposite side of the wound, configured to extend under a lowermost portion of said second anchor stitch and configured to extend up and then exit out of the tissue surface on a side of said second anchor stitch furthest from the wound edge at a closing stitch tissue exit point; and
      wherein the closing stitch includes a bound portion of the suture material configured to be disposed on the tissue surface to draw the wound to a closed condition, said bound portion of the closing stitch occupying a generally co-planar position relative to the bound portions of each of the first anchor stitch and second anchor stitch; and, the closing stitch is located close to the first connecting portion of the first anchor stitch at the closing stitch tissue insertion point; and, close to the second connecting portion of the second anchor stitch at the closing stitch tissue exit point to allow a conformational change in each of the first and second anchor stitches, wherein at least a part of the first connecting portion first anchor stitch that is located closest to the closing stitch is configured to move closer to a central longitudinal axis of the wound closure than each of the terminal ends of the first anchor stitch; and, at least a part of the second connecting portion of second anchor stitch that is located closest to the closing stitch is configured to move closer to the central longitudinal axis of the wound closure than at each of the terminal ends of the second anchor stitch, when the wound is drawn to the closed condition.

2. A surgical lattice stitch as defined in claim 1, and further comprising a plurality of first and second anchor stitches arranged in spaced end-to-end configurations on opposite sides of said wound, respectively.

3. A surgical lattice stitch as defined in claim 2, and further comprising a plurality of closing stitches tied between opposed pairs of first and second anchor stitches, respectively.

4. A surgical lattice stitch as defined in claim 3, wherein a second closing stitch is tied between said first anchor stitches and one of said second anchor stitches other than a second anchor stitch opposite said first anchor stitches.

5. A surgical lattice stitch as defined in claim 1, wherein a plurality of second closing stitches are tied between an opposed pair of first and second anchor stitches.

6. A surgical lattice stitch as defined in claim 1, and further comprising a plurality of first and second anchor stitches arranged in spaced relation with the end of one first and second anchor stitch overlapping the end of an adjacent first and second anchor stitch, respectively.

7. A surgical lattice stitch as defined in claim 6, wherein a second closing stitch is tied between said first anchor stitches and one of said second anchor stitches other than a second anchor stitch opposite said first anchor stitches.

8. A surgical lattice stitch as defined in claim 1, wherein said anchor and closing stitches are formed of a flexible, non-absorbable suture material.

9. A surgical lattice stitch as defined in claim 1, further comprising a tension limiting device configured to be disposed between at least one of said first and second anchor stitches and the surface of a tissue layer adjacent to the wound, said tension limiting device preventing over tensioning of said at least one of said first and second anchor stitches.

10. A surgical lattice stitch as defined in claim 9, wherein said tension limiting device is fenestrated.

11. A surgical lattice stitch as defined in claim 10, wherein said tension limiting device has a lower surface containing at least one horizontal groove between at least two fenestrations.

12. A surgical lattice stitch as defined in claim 10, wherein said tension limiting device is formed with a solid layer of material on at least one side thereof that can be penetrated by a suture needle.

13. A surgical lattice stitch as defined in claim 12, wherein said tension limiting device is impregnated with medications.

14. A surgical lattice stitch as defined in claim 10, wherein said tension limiting device is formed with a solid/semi-solid composite layer of material on at least one side of the device that can be penetrated by a suture needle.

15. A surgical lattice stitch as defined in claim 14, wherein said tension limiting device is impregnated with medications.

16. A surgical lattice stitch as defined in claim 9, wherein said tension limiting device is formed of a solid material which can be penetrated by a suture needle.

17. A surgical lattice stitch as defined in claim 9, wherein said tension limiting device has an upper surface containing a longitudinal groove for receiving and retaining a portion of the anchor stitch.

18. A surgical lattice stitch as defined in claim 9, wherein said tension limiting device has an upper surface containing at least one groove for receiving and retaining a portion of the closing stitch.

19. A surgical lattice stitch as defined in claim 9, wherein said tension limiting device contains at least two fenestrations and at least one notch in the peripheral edge thereof, said at least one notch located between said at least two fenestrations and configured to receive and retain a portion of the suture material.

20. A surgical lattice stitch as defined in claim 9, wherein said tension limiting device is formed of polymer material.

21. A surgical lattice stitch as defined in claim 9, wherein said tension limiting device is formed of reinforced polymer material.

22. A surgical lattice stitch as defined in claim 9, wherein said tension limiting device is formed of a composite material.

23. A surgical lattice stitch as defined in claim 9, wherein said tension limiting device is formed with an exterior encasement layer.

24. A surgical lattice stitch as defined in claim 9, wherein said tension limiting device is impregnated with medications.

25. A surgical lattice stitch as defined in claim 9, wherein said tension limiting device includes an adhesive layer on at least one side of the tension limiting device.

26. A method for suturing wounds, comprising the steps of
(a) inserting a first anchor stitch in a tissue layer spaced from and generally parallel to a wound;
(b) inserting a second anchor stitch in the tissue layer spaced from and generally parallel to the wound on an opposite side of the wound from said first anchor stitch; and
(c) tying a closing stitch formed of a suture material, inserted into the tissue layer and looped around said first and second anchor stitches in order to draw the wound to a closed condition; and
including one of (1) then, passing the suture material under a lowermost portion of said first anchor stitch, then, across the vertical plane of the wound to the opposite side of the wound, then under a lowermost portion of said second anchor stitch and up and out of the tissues on a side of said second anchor stitch furthest from an edge of the wound, (2) then, passing the suture material under a lowermost portion of said first anchor stitch, then, across the vertical plane of the wound to the opposite side of the wound, then, through a loop of said second anchor stitch and up and out of the tissues on a side of said second anchor stitch furthest from an edge of the wound, (3) then, passing the suture material through a loop of said first anchor stitch, then across the vertical plane of the wound to the opposite side of the wound, then under a lowermost portion of said second anchor stitch, then up and out of the tissues on a side of said second anchor stitch furthest from an edge of the wound, and (4) then, passing the suture material through a loop of said first anchor stitch, then across the vertical plane of the wound to the opposite side of the wound, then through a loop of said second anchor stitch, then up and out of the tissues on a side of said second anchor stitch furthest from an edge of the wound; and
then, tying the suture material at an upper surface of the tissue to draw the wound to a closed condition.

27. A method as defined in claim 26, and further comprising the step of inserting a plurality of first and second anchor stitches in spaced end-to-end configuration on opposite sides of said wound, respectively.

28. A method as defined in claim 27, and further comprising the step of tying a plurality of closing stitches between opposed pairs of first and second anchor stitches.

29. A method as defined in claim 28, and further comprising the step of tying a second closing stitch between a first anchor stitch and one of said second anchor stitches other than a second anchor stitch opposite said first anchor stitch.

30. A method as defined in claim 26, and further comprising the step of tying a plurality of closing stitches between an opposed pair of first and second anchor stitches.

31. A method as defined in claim 26, and further comprising the step of inserting a plurality of first and second anchor stitches arranged in spaced relation with the end of one first and second anchor stitch overlapping the end of an adjacent first and second anchor stitch, respectively.

32. A method as defined in claim 31, and further comprising the step of tying a second closing stitch between a first anchor stitch and one of said second anchor stitches other than a second anchor stitch opposite said first anchor stitch.

33. A method as defined in claim 26, and further comprising the step of inserting a tension limiting device between at least one of said first and second anchor stitches and the surface of a tissue layer adjacent the wound, said tension limiting device to prevent over-tensioning of said at least one of said first and second anchor stitches.

34. A lattice stitch tension limiting device, comprising:
a flexible elongated member configured to be positioned on an upper surface of a tissue layer between at least one anchor stitch and a wound, wherein a longitudinal axis of said member is positioned parallel with a longitudinal axis of the wound, and
said member containing at least two fenestrations for receiving suture thread used to form a lattice stitch, wherein a mouth of each of the fenestrations is disposed on a lower surface of the member, the mouth having a smooth surface, and configured to contact with the upper surface of the tissue layer, and
said member containing at least one notch in the peripheral edge thereof, said at least one notch located between said at least two fenestrations and configured to receive and retain a portion of the suture thread, and
said member configured to be displaced freely on the upper surface of the tissue layer due to forces exerted by the suture thread on said member,
wherein a central portion of said member having the mouths is configured to move in a plane parallel to the upper and lower surface of said member in a direction perpendicular to the longitudinal axis of said member in a direction toward the wound, when the lattice stitched is tied in a closed position.

35. A lattice stitch tension limiting device as defined in claim 34, wherein said member has an upper surface containing a longitudinal groove for receiving and retaining a portion of the anchor stitch.

36. A lattice stitch tension limiting device as defined in claim 34, wherein said member has an upper surface containing at least one groove for receiving and retaining a portion of the closing stitch.

37. A lattice stitch tension limiting device as defined in claim 34, wherein said member has at least one groove between said fenestrations.

38. A lattice stitch tension limiting device as defined in claim 34, wherein said member is formed of a polymer material.

39. A lattice stitch tension limiting device as defined in claim 34, wherein said member is formed of a reinforced polymer material.

40. A lattice stitch tension limiting device as defined in claim 34, wherein said member is formed of a composite material.

41. A lattice stitch tension limiting device as defined in claim 34, wherein said member is formed with an exterior encasement layer.

42. A lattice stitch tension limiting device as defined in claim 34, wherein said member is formed with a solid layer of material on one side thereof for contact with the tissue layer, said material being penetrable by a suture needle.

43. A lattice stitch tension limiting device as defined in claim 42, wherein said member is impregnated with medications.

44. A lattice stitch tension limiting device as defined in claim 34, wherein said member is formed with a solid/semi-solid composite layer of material on at least one side thereof for contact with the tissue layer, said material being penetrable by a suture needle.

45. A lattice stitch tension limiting device as defined in claim 44, wherein said member is impregnated with medications.

46. A lattice stitch tension limiting device as defined in claim 34, wherein said member includes an adhesive material attached to at least one side thereof.

47. A lattice stitch tension limiting device as defined in claim 34, wherein said member is impregnated with medications.

48. A lattice stitch tension limiting device as defined in claim 34, wherein said member contains at least one fenestration with an oval configuration.

49. A lattice stitch tension limiting device as defined in claim 34, wherein said member contains a plurality of fenestrations having a common major axis corresponding with the longitudinal axis of said member.

50. A lattice stitch tension limiting device as defined in claim 49, wherein said member contains a plurality of rows of fenestrations arranged in parallel to a common major axis corresponding with the longitudinal axis of said member.

51. A surgical lattice stitch repair adapted for closing wounds comprising three lengths of suture configured in the following arrangement:
(a) a first length of suture designated as a first anchor stitch configured to be arranged in a tissue layer parallel to and apart from a plane extending vertically through a first edge of a wound, said first anchor stitch configured to be bound in a closed loop at a fastening point located on a tissue surface; said first anchor stitch loop defined by a first anchor stitch loop tissue insertion point portion and a first anchor stitch loop tissue exit point portion, each of said first anchor stitch loop insertion point portion and first anchor stitch loop exit point portion representing a terminal end of the first anchor stitch loop on the tissue surface; said first anchor stitch loop further defined by a first connecting portion of suture located between the first anchor stitch tissue insertion point portion and the first anchor stitch tissue exit point portion;
(b) a second length of suture designated as a second anchor stitch configured to be arranged in the tissue layer parallel to and apart from the plane extending vertically through a second edge of the wound on an opposite side of the wound from said first anchor stitch, said second anchor stitch configured to be bound in a closed loop at a second fastening point located on the tissue surface; said second anchor stitch loop defined by a second anchor stitch loop tissue insertion point portion and a second anchor stitch loop tissue exit point portion, each of the second anchor stitch loop tissue insertion point portion and the second anchor stitch loop tissue exit point portion representing a terminal end of the second anchor stitch loop on the tissue surface; said second anchor stitch loop further defined by a second connecting portion of suture located between the second anchor stitch tissue insertion point portion and the second anchor stitch tissue exit point portion; and
(c) a third length of suture designated as a closing stitch configured to be inserted into the tissue surface at a closing stitch tissue insertion point and looped around said first anchor stitch and said second anchor stitch in order to draw the wound to a closed condition to provide a wound closure; and
the closing stitch including one of (1) configured to extend under a lowermost portion of said first anchor stitch, configured to extend across the vertical plane of the wound to the opposite side of the wound, under a lowermost portion of said second anchor stitch and configured to extend up and then exit out of the tissue surface on a side of said second length of suture furthest from the second edge of the wound at a closing stitch tissue exit point, (2) configured to extend under a lowermost portion of said first anchor stitch loop, configured to extend across the vertical plane of the wound to the opposite side of the wound, through a loop of said second anchor stitch and configured to extend up and then exit out of the tissue surface on a side of said second anchor stitch furthest from the second edge of the wound at a closing stitch tissue exit point, and (3) configured to extend through a loop of said first anchor stitch, configured to extend across the vertical plane of the wound to the opposite side of the wound, under a lower most portion of said second anchor stitch, then configured to extend up and then exit out of the tissue surface on a side of said second anchor stitch furthest from the second edge of the wound at a closing stitch tissue exit point; and wherein the closing stitch includes a bound portion of the suture material configured to be disposed on the tissue surface to draw the wound to a closed condition, said bound portion of the closing stitch occupying a generally co-planar position relative to the bound portions of each of the first anchor stitch and second anchor stitch; and, the closing stitch is located close to the first connecting portion of the first anchor stitch at the closing stitch tissue insertion point, and close to the second connecting portion of the second anchor stitch at the closing stitch tissue exit point to allow a conformational change in each of the first and second anchor stitches, wherein at least a part of the first connecting portion of the first anchor stitch that is located closest to the closing stitch is configured to move closer to a central longitudinal axis of wound closure than each terminal end of the first anchor stitch; and, at least a part of the second connecting portion of the second anchor stitch that is located closest to the closing stitch is configured to move closer to the central longitudinal axis of wound closure than each terminal end of the second anchor stitch; when the wound is drawn to the closed condition.

52. A surgical lattice stitch as defined in claim 51, further comprising a tension limiting device configured to be disposed between at least one of said first and second anchor stitches and the surface of a tissue layer adjacent to the wound, said tension limiting device preventing over-tensioning of said at least one of said first and second anchor stitches.

* * * * *